(12) United States Patent
Beebe et al.

(10) Patent No.: US 7,253,003 B2
(45) Date of Patent: Aug. 7, 2007

(54) METHOD FOR MONITORING THE ENVIRONMENT WITHIN A MICROFLUIDIC DEVICE

(75) Inventors: David J. Beebe, Madison, WI (US); Jaisree Moorthy, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 244 days.

(21) Appl. No.: 10/045,937

(22) Filed: Oct. 19, 2001

(65) Prior Publication Data

US 2003/0077836 A1   Apr. 24, 2003

(51) Int. Cl.
*G01N 33/48* (2006.01)
(52) U.S. Cl. .................... 436/164; 436/163; 436/166; 436/169; 422/58; 422/61; 435/288.7; 435/287.2
(58) Field of Classification Search ............... 422/56, 422/58, 61, 99, 102, 103; 436/164, 163, 436/1, 166, 169; 435/288.7, 287.2
See application file for complete search history.

(56) References Cited

U.S. PATENT DOCUMENTS

| 4,149,852 | A | * | 4/1979 | Tiru et al. ................. 436/163 |
| 6,159,686 | A | | 12/2000 | Kardos et al. .................. 435/6 |
| 6,277,641 | B1 | | 8/2001 | Yager .......................... 436/52 |
| 6,297,061 | B1 | | 10/2001 | Wu et al. .................... 436/518 |
| 6,306,590 | B1 | | 10/2001 | Mehta et al. .................... 435/6 |
| 6,316,267 | B1 | | 11/2001 | Bhalgat et al. ............... 436/86 |
| 6,488,872 | B1 | * | 12/2002 | Beebe et al. .................. 264/31 |
| 6,589,779 | B1 | * | 7/2003 | McDevitt et al. ......... 435/288.7 |
| 2003/0064422 | A1 | * | 4/2003 | McDevitt et al. .......... 435/7.32 |

\* cited by examiner

*Primary Examiner*—Lyle A. Alexander
(74) *Attorney, Agent, or Firm*—Boyle Fredrickson Newholm Stein & Gratz S.C.

(57) ABSTRACT

A method and apparatus is provided for monitoring the environment within a microfluidic device. The microfluidic device includes a body defining a channel for accommodating flow of fluid therethrough. A monitor structure is disposed in the channel of the body in the flow of fluid. The monitor structure changes color and/or dimension in response to various parameters of the fluid having predetermined values.

14 Claims, 3 Drawing Sheets

METHOD FOR MONITORING THE ENVIRONMENT WITHIN A MICROFLUIDIC DEVICE

REFERENCE TO GOVERNMENT GRANT

This invention was made with United States government support awarded by the following agencies: DOD ARPA F30602-00-2-0570. The United States has certain rights in this invention.

FIELD OF THE INVENTION

This invention relates generally to microfluidic devices, and in particular, to a method and apparatus for sensing changes in the microenvironment within a microfluidic device.

BACKGROUND AND SUMMARY OF THE INVENTION

As is known, microfluidic systems are being used in an increasing number of applications, including biological applications. In order to perform these applications, microfluidic systems must carry out various types of functions such as sample purification, separation and detection. These functions, in turn, require the development of various microfluidic components such as filters, valves and detectors and the incorporation of the components into an integrated microfluidic system.

A typical detector consists of a sensor to test the sample within the microenvironment of a microfluidic device and a display unit to present the results of such test. In order to detect and monitor the environment inside these micron-sized devices, several sensitive methods have been contemplated including conductivity measurement, UV-visible spectroscopy and fluorescence spectroscopy. It can be appreciated that such methods are usually associated with complex instrumentation thereby making fabrication of the corresponding microfluidic systems difficult. In addition, operating such complex instrumentation often requires significant power, and hence, utilization of power sources such as batteries or the like. These power sources may be considerably larger than the microfluidic device itself, rendering the microfluidic system too heavy or too large to be attractive to potential users.

For certain applications like evaluating the purity of water or finding the pH range for a sample of fluid, detecting the existence of a change is more important than the extent of the change. Further, in other applications, the precise quantitative results may not be as important as the rapid detection ability and/or the portability of the system. For example, quickly obtaining the results from a pregnancy or diabetes test may be more important to a user than the precise quantitative results.

Therefore, it is a primary object and feature of the present invention to provide an apparatus for sensing changes in the micro-environment within a microfluidic device that does not require utilization of power sources such as batteries or the like.

It is a further object and feature of the present invention to provide a method and apparatus for monitoring the environment within a microfluidic device that quickly detects the change of the environment within the microfluidic device.

It is a still further object and feature of the present invention to provide a method and apparatus for monitoring the environment within a microfluidic device that is simple and inexpensive.

In accordance with the present invention, a microfluidic device is provided for displaying indicia in response to a change in the predetermined parameter of a fluid flowing therethrough. The microfluidic device includes a body member defining a channel accommodating the flow of the fluid therethrough. A monitor structure is proposed in the channel of the body in the flow of fluid. The monitor structure displays a first indicia in response to a predetermined parameter of the fluid having the first value and a second indicia in response to the predetermined parameter of the fluid having a second value.

The monitor structure includes a polymerized mixture. The polymerized mixture includes an immobilized dye which is a first color in response to the predetermined parameter of the fluid having the first value and which is a second color in response to the predetermined value of the fluid having the second value. It is contemplated that the first indicia displayed by the monitor structure is provided by the dye being the first color and the second indicia displayed the monitor structure is provided by the dye being the second color. The dye may be phenolphthalein or congo red.

The mixture may include a hydrogel, a photoinitiator and a cross-linker. It is contemplated that the polymerized mixture have a first dimension in response to the predetermined parameter of the fluid having the first value and a second dimension in response to the predetermined parameter of the fluid having a second value. In such circumstances, the first indicia displayed by the monitor structure is provided by the polymerized mixture being the first dimension and the second indicia displayed by the monitor structure is provided by the polymerized mixture being the second dimension.

The microfluidic device may also include a second monitor structure disposed in the channel of the body in the flow of fluid. The second monitoring structure provides a first indicia in response to a second predetermined parameter of the fluid having a first value and second indicia in response to the second predetermined parameter of the fluid having a second value.

In accordance with a further aspect of the present invention, a method is provided for monitoring an environment within a microfluidic device. The method includes the steps of providing a monitor structure in a channel of the microfluidic device and passing fluid over the monitor structure in the channel. The monitor structure generates a visual display in response to exposure to a parameter of the fluid having a predetermined value.

In order to provide the monitor structure, a dye is immobilized in a polymer matrix. This is provided by mixing the dye in a prepolymer mixture and providing the same as a pregel. The pregel is injected in the channel and polymerized in the channel to form the monitor structure. Thereafter, the channel of the microfluidic device is cleaned.

The pre-polymer mixture includes a hydrogel, photoinitiator and a cross-linker. More specifically, the pre-polymer mixture may 2-hydroxy ethyl methacrylate (HEMA), acrylic acid (AA), ethylene glycol dimethacrylate (EGDMA), and 2,2-dimethoxy-2-phenylacetophenone (DMPA). The dye may be phenolphthalein or congo red.

The method of the present invention may also include the additional steps of providing a second monitor structure in the microfluidic device and passing fluid over the second monitor structure in the channel. The second monitor structure generates a visual display in response to exposure to the second parameter of the fluid having a predetermined value.

In accordance with a still further aspect of the present invention, a method is provided for monitoring the environment within a microfluidic device. The method includes the steps of mixing a dye in a pre-polymer mixture and providing the same as a pregel. The pregel is injected into a channel of the microfluidic device and polymerized therein to form a monitoring structure. The fluid is passed over the monitoring structure in the channel such that the dye changes color in response to the parameter of the fluid having the predetermined value. When the pregel is polymerized within the channel, the dye is immobilized in the polymerized mixture. The dye may be phenolphthalein or congo red. The pre-polymer mixture may include a hydrogel, a photo-initiator and a cross-linker. More specifically, the pre-polymer mixture may include 2-hydroxy ethyl methacrylate (HEMA), acrylic acid (AA), ethylene glycol dimethacrylate (EGDMA), and 2,2-dimethoxy-2-phenylacetophenone (DMPA).

It is contemplated that the monitor structure change dimension in response to the predetermined value of the second parameter of the fluid. In addition, a second monitor structure may be provided in the channel. Fluid is passed over the second monitor structure such that the second monitor structure changes color in response to a second parameter of the fluid having a predetermined value. The second monitor structure may be fabricated by mixing a second dye in a second pre-polymer mixture and providing the same as a second pregel. The second pregel is injected into the channel of the microfluidic device and polymerized therein so as to form the second monitor structure. After the first and second pregels are polymerized in the channel, the channel of the microfluidic device is cleaned.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
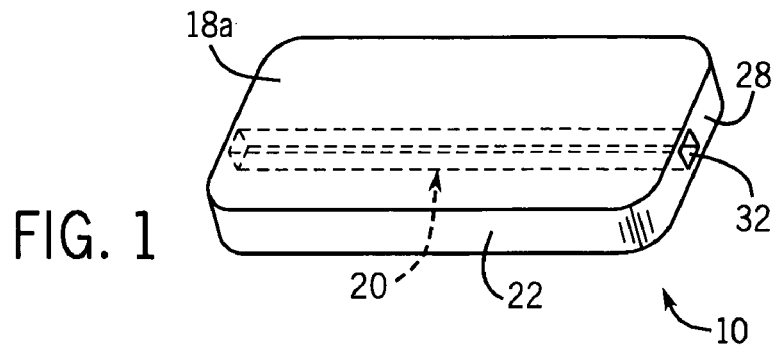
FIG. 1 is an isometric view of a microfluidic device in accordance with the present invention.
Figure 2:
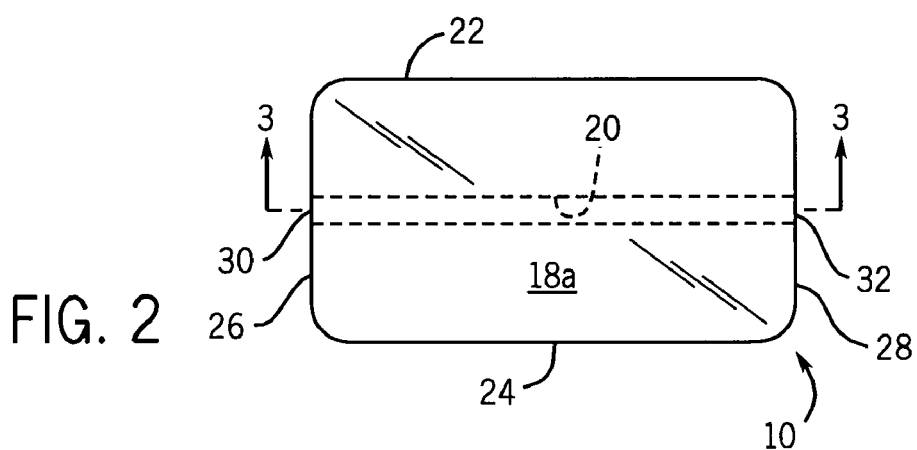
FIG. 2 is a top plan view of the microfluidic device of FIG. 1.
Figure 3:
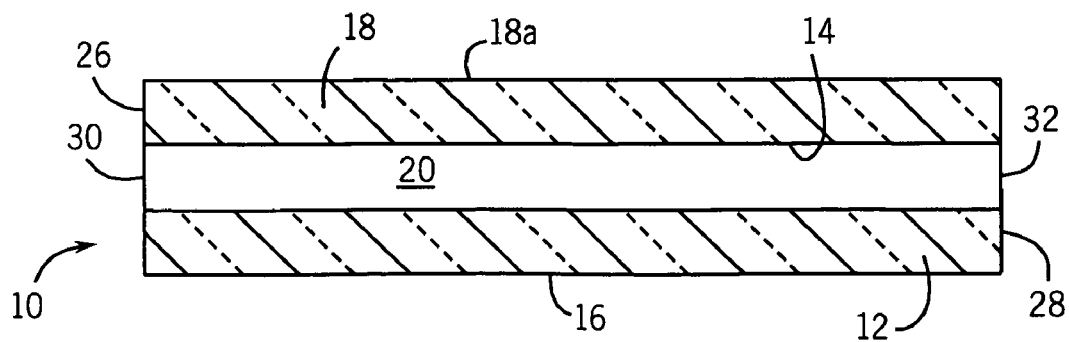
FIG. 3 is a cross-sectional view of the microfluidic device taken along line 3-3 of FIG. 2.

Referring to FIGS. 1-5, a microfluidic device in accordance with the present invention is generally designated by the reference numeral 10. Microfluidic device 10 is defined by a body 12 having upper and lower surfaces 14 and 16, respectively, and by a cover 18 affixed to upper surface 14 of body 12 by an optical adhesive. Upper surface 14 of body 12 includes a channel 20 etched therein using any suitable micro-machining technique. During assembly, microfluidic device 10 is cured with ultraviolet radiation for a predetermined time period (e.g. 45-60 seconds), depending upon the depth of the channel 20, and thereafter, baked (e.g. at 50 Celsius for approximately 10 hours) to remove any solvent from the optical adhesive.

In its assembled configuration, microfluidic device 10 includes first and second sides 22 and 24, respectively, and first and second ends 26 and 28, respectively. Channel 20 is generally linear and includes an input port 30 at first end 26 of microfluidic device 10 and an output port 32 at second end 28 of microfluidic device 10. It is intended that fluid flow though channel 20 from input port 30 to output port 32.

Figure 9:
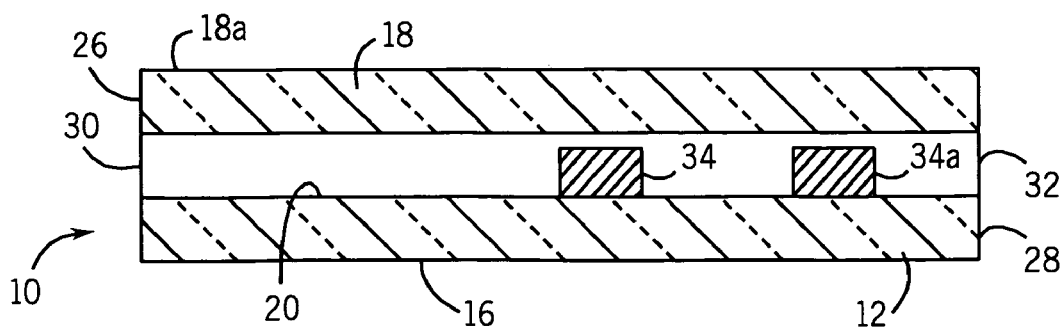
FIG. 9 is a cross-sectional view of a microfluidic device incorporating first and second monitoring structures fabricated according to the method of the present invention.

As hereinafter described, one or more readout or monitor structures 34 and 34a, FIG. 9, are fabricated inside channel 20 of microfluidic device 10. It is intended that each monitor structure 34 and 34a function as both a sensor and a display unit. Monitor structures 34 and 34a work autonomously on basic calorimetric principles. Any chemical change in the fluid flowing through channel 20 is manifested in a change in color of one or both of monitor structures 34 and 34a. The color changes of monitor structures 34 and 34a can be seen directly by the human eye without the need of any instrumentation. Rapid signal processing by our vision system allows the changes in color of monitor structures 34 and 34a to be perceived instantaneously and interpreted intelligently. Monitor structures 34 and 34a are formed from ion-sensitive dyes immobilized in polymer matrixes. It is intended that the term "dye," as hereinafter provided, encompass any substance that can be fixed in a polymer matrix, such a gel, and that produces a visible change in response to some stimuli. The color change of dyes, and hence of the monitor structures 34 and 34a, are induced by the presence of specific ions. In addition, it is contemplated that the polymer matrixes be formed from a hydrogel such that the dimensions of monitor structures 34 and 34a are affected by stimuli like chemicals, temperature or electric field. Consequently, the changes in the environment within channel 20 may be reflected in the size and color of monitor structures 34 and 34a.

Figure 4:
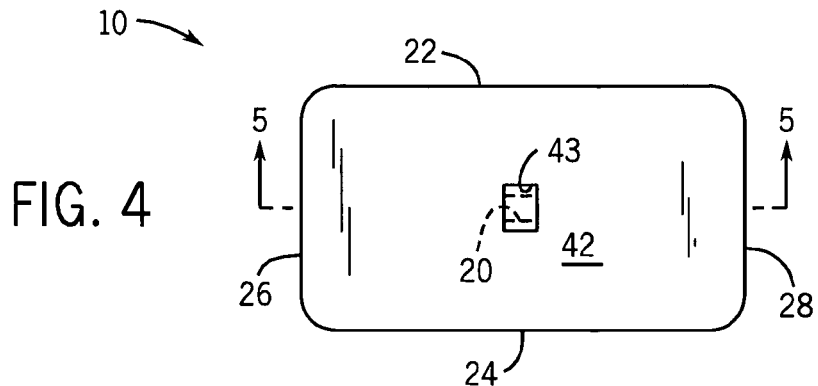
FIG. 4 is a top plan view of the microfluidic device of FIG. 1 having an optical mask affixed to the upper surface thereof.
Figure 5:
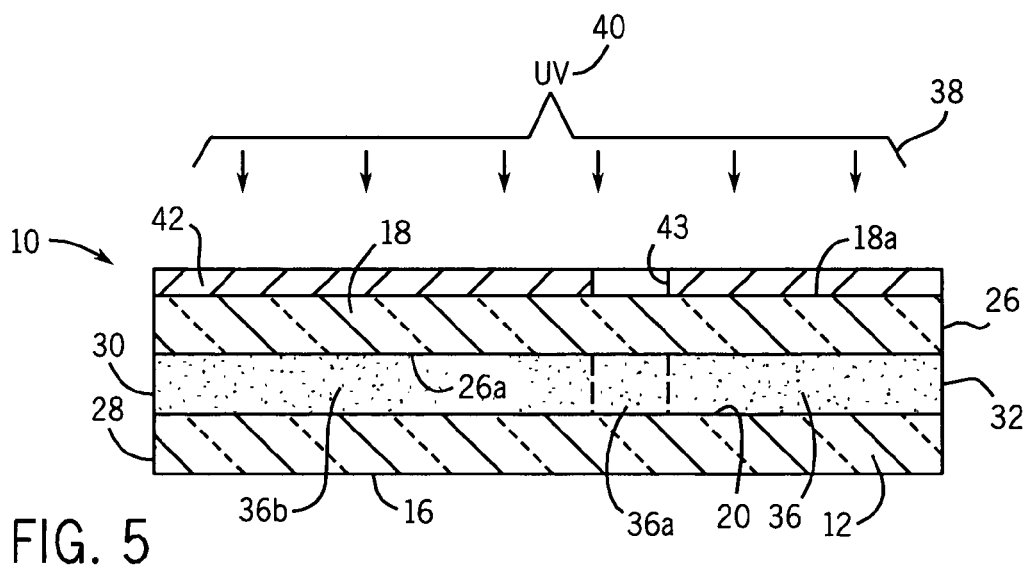
FIG. 5 is a cross-sectional view of the microfluidic device taken along line 5-5 of FIG. 4 showing polymerization of a portion of a mixture within the channel of the microfluidic device.
Figure 6:
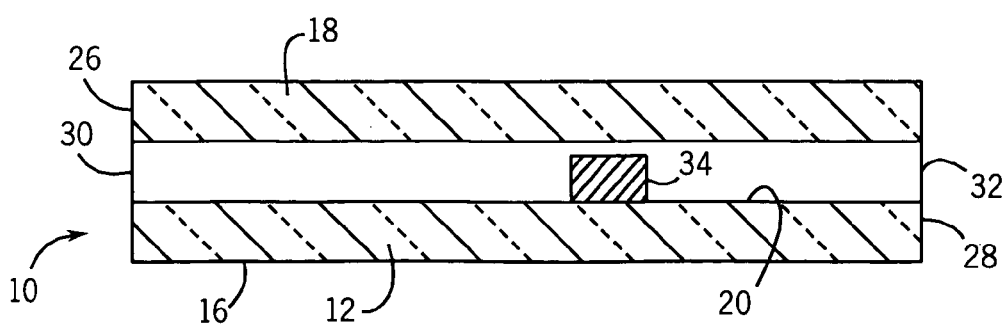
FIG. 6 is a cross-sectional view of the microfluidic device incorporating a monitor structure fabricated according to the method of the present invention.

By way of example, monitor structure 34 is formed by physically entrapping congo red (CR) dye powder, a pH sensitive dye, in a polymer matrix such as a hydrogel, FIGS. 4-6. Monitor structure 34a is formed by physically entrapping phenolphthalein (PP) dye powder, a pH sensitive dye, in a polymer matrix such as a hydrogel, FIGS. 7-9. It can be appreciated that monitor structures 34 and 34a may be fabricated from other types of dye powers and other types of polymers without deviating from the scope of the present invention.

Referring back to FIGS. 4-6, CR is a dye powder that was introduced in 1884 for dyeing cotton. The low resistance to washing and sunlight did not make CR popular for dyeing clothes. In recent years, CR has become a commonly used dye for staining in cellulose and amyloid studies and as a pH indicator. The pKa 1 of the dye is 4, which accounts for the transition of CR from blue to red color between 3.0 and 5.0 pH.

The polymer matrix is prepared from the co-polymerization of a hydrogel such as HEMA (2-hydroxyethyl methacrylate) and AA (acrylic acid). The acidic functionality of AA makes the polymer matrix pH sensitive i.e. swell in high pH solution. A small quantity of a cross-linker such as EGDMA (ethylene glycol dimethacrylate) is included to provide mechanical strength to the polymer matrix. As is known, the polymerization of the hydrogel occurs via formation of radicals. As such, a photo-initiator such as DMPA (2,2-dimethoxy-2-phenyl-acetophenone) is added to the polymer matrix so that radicals can be generated by irradiation with ultraviolet light and to facilitate photo-patterning of the monitor structure 34.

In order to fabricate monitor structure 34 in channel 20, a CR pregel 36 prepared by mixing the CR dye (10% by wt in powder form) in the pH responsive pre-polymer mixture including HEMA, AA, EGDMA and DMPA (weight ratio 2.7822:0.3851:0.0317:0.0950). After a thorough mixing, the CR pregel 36 is injected into channel 20 at a user desired location. As best seen in FIG. 5, polymerizable stimulus such as temperature or an ultraviolet source 40 is positioned above upper surface 18a of cover 18 of microfluidic device 10. Ultraviolet source 40 generates ultraviolet light, generally designated by the reference numeral 38, which is directed towards microfluidic device 10 at an angle generally perpendicular to upper surface 18a of cover 18. An optical mask 42 is affixed to upper surface 18a of cover 18. Optical mask 42 includes an opening 43 therein corresponding to the desired shape and location of monitor structure 34 to be formed in channel 20.

It can be appreciated that a first portion 36a of CR pregel 36 is exposed to ultraviolet light 38 generated by ultraviolet source 40, while a second portion 36b of CR pregel 36 is shielded from ultraviolet light 38 generated by ultraviolet source 40 by optical mask 42. The exposed portion 36a of CR pregel 36 polymerizes and solidifies when exposed to ultraviolet light 38 generated by ultraviolet source 40. The exposed portion 36a of CR pregel 36 is polymerized for a predetermined time period (i.e. 3 minutes) using ultraviolet light 38 generated by ultraviolet source 40 so as to form monitor structure 34.

It is contemplated that the intensity of the ultraviolet light 38 be approximately 3.5 mW/cm$^2$ at 3 inches away. However, other intensities are possible without deviating from the scope of the present invention. In addition, it is possible to fabricate an array of monitor structures 34 by placing an alternate mask 42 with a photo-pattern thereon between channel 20 and ultraviolet source 40. After monitor structure 34 is polymerized, channel 20 is flushed (e.g. with methanol and water) and dried (e.g. by baking at 45 Celsius for 10 hours).

Figure 7:
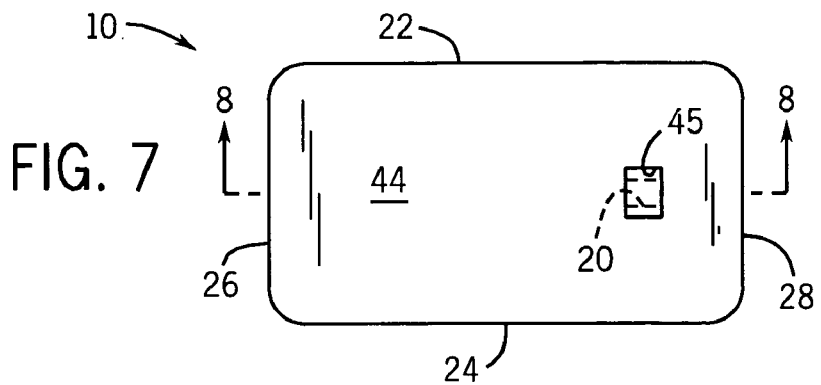
FIG. 7 is a top plan view of the microfluidic device of FIG. 1 having a second optical mask affixed to the upper surface thereof.
Figure 8:
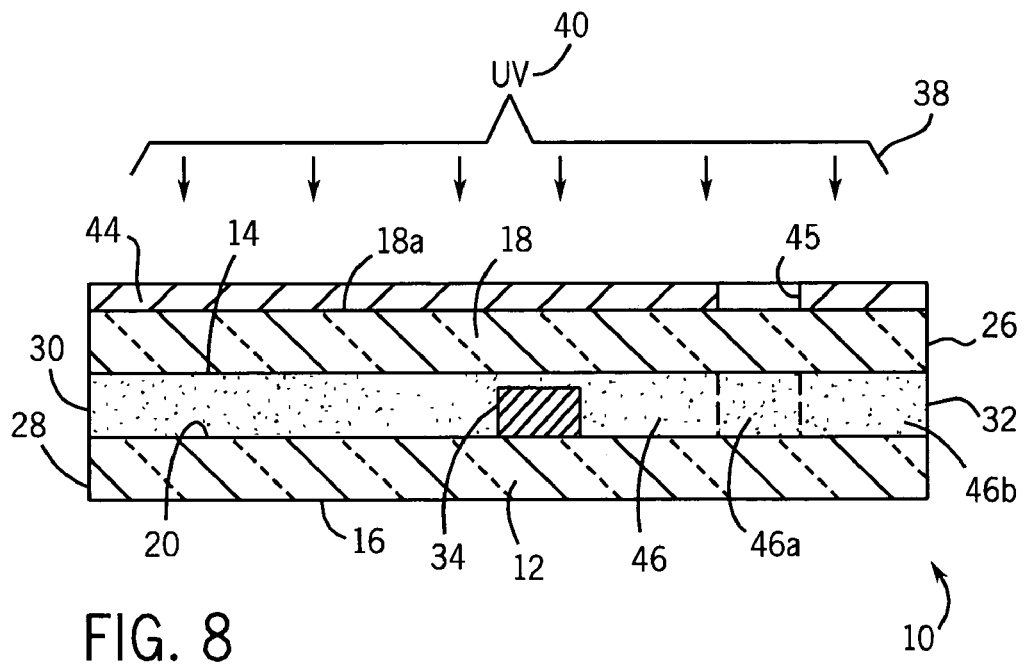
FIG. 8 is a cross-sectional view of the microfluidic device taken along line 8-8 of FIG. 7 showing polymerization of a portion of a second mixture within the channel of the microfluidic device.

Referring to FIGS. 7-9, in order to fabricate monitor structure 34a, PP dye powder is substituted for the CR dye powder used to fabricate monitor structure 34. PP is a commonly used pH indicator dye powder. In its ionized form, PP is pink in color while colorless in its neutral form. The pKa of PP is 9.1, which explains the transition of color at around 8-9.6 pH. A PP pregel 46 is prepared by mixing the PP dye (10% by wt in powder form) in the pH responsive pre-polymer mixture including HEMA, AA, EGDMA and DMPA (weight ratio 2.7822:0.3851:0.0317:0.0950). After a thorough mixing, the PP pregel 46 is injected into channel 20 at a second user desired location. As best seen in FIG. 8, a polymerizable stimulus such as temperature or ultraviolet source 40 is positioned above upper surface 18a of cover 18 of microfluidic device 10. Ultraviolet source 40 generates ultraviolet light 38, which is directed towards microfluidic device 10 at an angle generally perpendicular to upper surface 18a of cover 18. An optical mask 44 is affixed to upper surface 18a of cover 18. Optical mask 44 includes an opening 45 therein corresponding to desired shape and location of monitor structure 34 to be formed in channel 20.

It can be appreciated that a first portion 46a of PP pregel 46 is exposed to ultraviolet light 38 generated by ultraviolet source 40, while a second portion 46b of PP pregel 46 is shielded from ultraviolet light 38 generated by ultraviolet source 40 by optical mask 44. The exposed portion 46a of PP pregel 46 polymerizes and solidifies when exposed to ultraviolet light 38 generated by ultraviolet source 40. The exposed portion 46a of PP pregel 46 is polymerized for a predetermined time period (i.e. 45-50 seconds) using ultraviolet light 38 generated by ultraviolet source 40 so as to form monitor structure 34a. It is contemplated that the intensity of the ultraviolet light 38 be approximately 3.5 mW/cm$^2$ at 3 inches away. However, other intensities are possible without deviating from the scope of the present invention. In addition, it is possible to fabricate an array of monitor structures 34a by placing an alternate second mask 44 with a photo-pattern thereon between channel 20 and UV light source 40. After monitor structure 34a is polymerized, channel 20 is flushed (e.g. with methanol and water) and dried (e.g. by baking at 45 Celsius for 10 hours).

The lateral (length and width) dimensions of monitor structures 34 and 34a are limited by the resolution of masks 42 and 44, respectively. Also, the heights of monitor structures 34 and 34a are dependent on the absorbance of the dyes used since the intensity of the ultraviolet radiation decreases exponentially with the distance through the pregels. For example, CR dye absorbs ultraviolet radiation in the same region as the photo-initiator.

After monitor structures 34 and 34a are fabricated in channel 20 of microfluidic device 10, monitor structure 34 is red in color, while monitor structure 34a is colorless. If an acidic solution (low pH) flows though channel 20 and engages monitor structures 34 and 34a, monitor structure 34 turns blue and monitor structure 34a remains colorless. If a basic solution (high pH) flows though channel 20 and engages monitor structures 34 and 34a, monitor structures 34 and 34b swell to about twice their initial size. In addition, monitor structure 34 turns red and monitor structure 34a turns pink.

It can be appreciated that the performance of microfluidic device 10 depends on the choice of dyes and the polymer matrix used to create the monitor structures 34 and 34b. The ions of the fluid flowing though channel 20 of microfluidic device 10 must diffuse into the polymer matrix in order for the dye to change colors. Since the time for diffusion increases with the square of the distance transported, the size of monitor structures 34 and 34a must be relatively small in order to reduce the response time necessary for the colors of monitor structures 34 and 34a to change. While a large surface area will reduce response time, it is possible that when monitor structures 34 and 34a are placed too close together, monitor structures 34 and 34a may close off channel 20 when swelled. Such a design must be avoided, since the functioning of other microfluidic components placed in channel 20 downstream of monitor structures 34 and 34a can be impaired.

Further, the polymer matrix must not interact chemically with the ions of the fluid or form a physical barrier to diffusion, and the extent of cross-linking in the polymer matrix must be minimal to improve the response time. One way to achieve a less cross-linked polymer matrix is to expose the pre-polymer mixture to lower doses of ultraviolet radiation. Similarly, the choice of the dyes is critical as the dye molecules must not interact with the polymer chains selected. The accuracy of the results provided by monitor structures 34 and 34a is dependent on the sensitivity and selectivity of the dyes. For example, the dyes must not cross-react to prevent interference from other signals.

While the monitor structures 34 and 34a heretofore described are used to detect the pH level of the fluid flowing through channel 20, it can be understood that monitor structures 34 and 34a in channel 20 of microfluidic device 10 may be used in other applications. By way of example, monitor structures 34 and 34a may be used to continuously monitor the environmental conditions and products of a cell culture within channel 20 of microfluidic device 10. This application can be accomplished by simply altering the types of dyes and/or polymers utilized when fabricating monitor structures 34 and 34a.

Various modes of carrying out the invention are contemplated as being within the scope of the following claims particularly pointing out and distinctly claiming the subject matter that is regarded as the invention.

We claim:

1. A method for monitoring the environment within a microfluidic device, comprising the steps of:
   immobilizing a first monitor structure in a channel of the microfluidic device by:
      mixing a dye in a pre-polymer mixture to provide a pregel mixture;
      injecting the pregel in the channel of the microfluidic device; and
      polymerizing the pregel mixture in the channel to form the first monitor structure;
   passing fluid over the monitor structure in the channel;
   providing a second monitor structure in the channel of the microfluidic device; and
   passing fluid over the second monitor structure in the channel; whereby:
      the first monitor structure generates a visual display unrelated to a potential change in the size of the first monitor structure in response to exposure to a first parameter of the fluid; and
      the second monitor structure generates a visual display in response to exposure to a second parameter of the fluid.

2. The method of claim 1 comprising the additional step of cleaning the channel of the microfluidic device after polymerizing the pregel mixture.

3. The method of claim 1 wherein the pre-polymer mixture includes.

4. The method of claim 1 wherein the pre-polymer mixture includes 2-hydroxy ethyl methacrylate (HEMA), acrylic acid (AA), ethylene glycol dimethacrylate (EGDMA), and 2,2-dimethoxy-2-phenylacetophenone (DMPA).

5. The method of claim 1 wherein the dye is congo red.

6. The method of claim 1 wherein the dye is phenolphthalein.

7. A method for monitoring the environment within a micro fluidic device, comprising the steps of:
   mixing a dye in a pre-polymer mixture to provide a pregel mixture;
   injecting the pregel mixture into a channel of the microfluidic device;
   polymerizing the pregel mixture in the channel to form a first monitor structure;
   passing fluid over the first monitor structure in the channel such that the dye changes color in response to a parameter of the fluid; and
   passing fluid over a second monitor structure provided in the channel such that the second monitor structure changes color in response to a second parameter of the fluid.

8. The method of claim 7 wherein the monitor structure changes dimension in response to a predetermined value of a second parameter of the fluid.

9. The method of claim 7 comprising the additional step of cleaning the channel of the microfluidic device after polymerizing the pregel.

10. The method of claim 7 wherein the pre-polymer mixture includes a hydrogel, a photo-initiator and a cross-linker.

11. The method of claim 7 wherein the pre-polymer mixture includes 2-hydroxy ethyl methacrylate (HEMA), acrylic acid (AA), ethylene glycol dimethacrylate (EGDMA), and 2,2-dimethoxy-2-phenylacetophenone (DMPA).

12. The method of claim 7 wherein the dye is phenolphthalein.

13. The method of claim 7 wherein the dye is congo red.

14. The method of claim 7 comprising the additional steps of:
   mixing a second dye in a second pre-polymer mixture to provide a second pregel mixture;
   injecting the second pregel mixture into the channel of the microfluidic device; and
   polymerizing the second pregel mixture in the channel to form the second monitor structure.

* * * * *